US00PP35906P2

(12) United States Plant Patent
Knapp et al.

(10) Patent No.: US PP35,906 P2
(45) Date of Patent: Jul. 2, 2024

(54) STRAWBERRY PLANT NAMED 'UC ECLIPSE'

(50) Latin Name: ***Fragaria* x *ananassa* Duchesne**
Varietal Denomination: UC Eclipse

(71) Applicant: The Regents of the University of California, Oakland, CA (US)

(72) Inventors: Steven J. Knapp, Davis, CA (US); Glenn S. Cole, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/135,705

(22) Filed: Apr. 17, 2023

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209
CPC ... A01H 5/08; A01H 5/00; A01H 6/74; A01H 6/7409
See application file for complete search history.

(56) References Cited

U.S. PATENT DOCUMENTS

PP19,767 P2 * 2/2009 Shaw ..... A01H 5/08 Plt./209
PP19,975 P2 * 5/2009 Shaw ..... A01H 6/7409 Plt./209
PP26,709 P3 * 5/2016 Larson ..... A01H 5/08 Plt./208
PP34,242 P2 * 5/2022 Knapp ..... Plt./209

OTHER PUBLICATIONS

Cal Poly Strawberry Center 2022 Strawberry Field Day, retrieved online at https://content-calpoly-edu.s3.amazonaws.com/strawberry/1/images/2022FieldDayBooklet-FINAL_07_22_22-PM-comp.pdf, 6 introductory pages, pp. 20-29. (Year: 2022).*
See information in accompanying Information Disclosure Statement letter, 10 pp. 2020 and 8 pp. 2021.

* cited by examiner

*Primary Examiner* — June Hwu
(74) *Attorney, Agent, or Firm* — Kilpatrick Townsend & Stockton LLP

(57) ABSTRACT

'UC Eclipse' is a summer-plant cultivar strawberry plant that is *Fusarium* wilt-resistant and produces large, firm fruit throughout the growing season.

1 Drawing Sheet

Genus and species: The strawberry- plant of this invention is botanically known as *Fragaria* X *ananassa* Duchesne.

Variety denomination: The variety denomination is 'UC Eclipse'.

BACKGROUND

This invention relates to a new and distinct summer-plant cultivar of strawberry designated as 'VC Eclipse'. The plant of this selection was originally designated '17C242P023' for testing.

BRIEF SUMMARY

'UC Eclipse' is a day-neutral cultivar produced from a cross produced between 'Portola' (U.S. Plant Pat. No. 20,552) and 'UCD Mojo' (U.S. Plant Pat. No. 34,265) in the winter of 2017. It is unknown which is the female parent and which is the male parent. Clones (daughter plants) of 'UC Eclipse' were initially propagated from a single mother plant in 2018. 'UC Eclipse' has since been preserved by annual cycles of asexual propagation from stolons in a facility at Winters, California.

'UC Eclipse' was selected from a full-sib family (17C242) generated from the cross between 'Portola' and 'UCD Mojo'. Seeds of the 17C242 family were harvested in the spring of 2017 and germinated in June 2017. Seedlings were transplanted to a greenhouse in July 2017, hardened off in a shade house in August 2017, and transplanted to the field in September 2017. 'UC Eclipse' was one of 10,000 individual hybrid plants from 359 full-sib families that were grown in 2017-18). The population was visually phenotyped in the spring of 2018 to: (a) identify individuals with outstanding fruit size, firmness, symmetry, color, gloss, and visual appeal; (b) eliminate individuals with fruit defects and deformities; (c) estimate marketable fruit yields; (d) identify putative photoperiod insensitive individuals; (e) assess stolon proliferation (runner production) and plant architecture; and (f) select individuals for clonal multiplication and further testing. Twenty-five individuals from the 2017-18 selection cycle were selected for advanced testing (Phase I, II, and III) in Santa Maria, Ventura, and Lompoc, California. Disease resistance of the selections was tested in Davis, California.

'UC Eclipse' is a summer-plant cultivar that differs from parental and comparison varieties as follows: 'UC Eclipse' is Fusarium wilt-resistant compared to parental varieties 'UCD Mojo' and comparison variety 'UCD Finn' (U.S. Plant Pat. No. 34,242). 'UC Eclipse' also has firmer, larger fruit compared to parent variety 'Portola' and provides consistently higher yields compared to 'Portola', 'UCD Finn', and 'UCD Mojo'.

'UC Eclipse' was genotyped with a 50,000-SNP array (Hardigan et. al., *Frontiers in Plant Science* 10:1789, 2020; Hardigan et al., *Mol. Biol. Evol.* 38:2285-2305, 2021) that included 72 cultivars owned by the University of California and 300 publicly available cultivars not owned by the University of California. After quality- and LD-pruning, 30,671 SNP markers with well-separated codominant genotypic clusters were estimating genomic relationships. These analyses confirmed that 'UC Eclipse' is genetically distinct from its parents and comparison varieties 'UCD Mojo', 'Portola', and 'UCD Finn', as well as all of the other cultivars evaluated.

BRIEF DESCRIPTION OF THE DRAWINGS

The colors in the photograph are depicted as nearly true as is reasonably possible to obtain in color reproductions of this type.

DETAILED DESCRIPTION

Botanical Description

Figure 1:
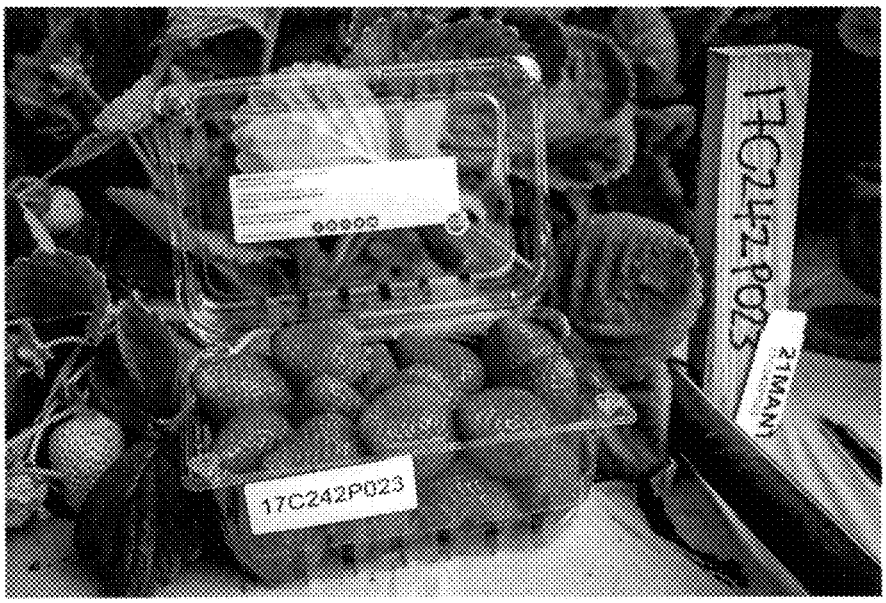
FIG. 1 depicts fruit of 'UC Eclipse'. Plants of 'UC Eclipse' with immature fruit are also shown.
Figure 2:
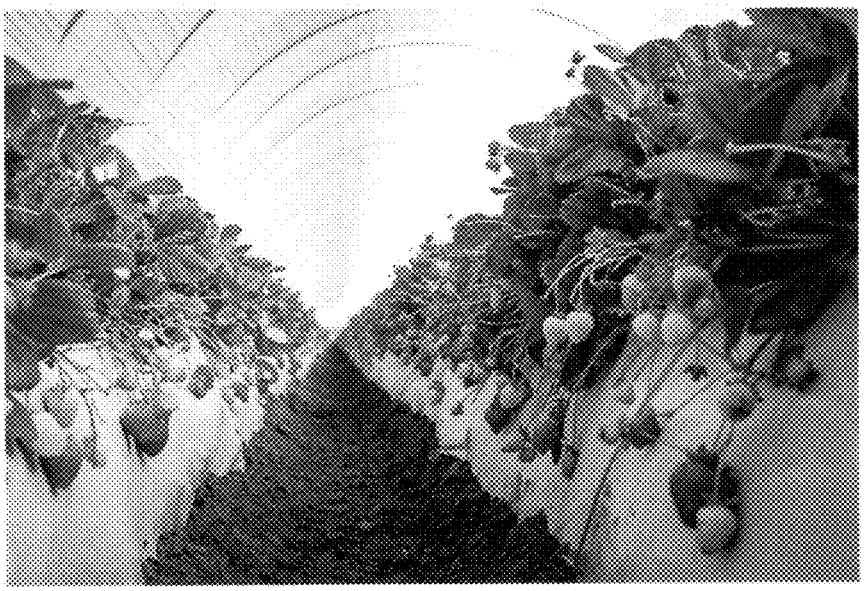
FIG. 2 shows 'UC Eclipse' plants.

Botanical descriptors of 'UC Eclipse' are provided in Table 1. The descriptors were collected in the spring and summer of 2022 from plants grown in Santa. Maria, California. Colors are designated with reference to The Royal Horticultural Society (R.H.S.) Colour Chart, Sixth Edition, 2015. The characteristics of 'UC Eclipse' may vary in detail, depending upon environmental factors and culture conditions.

TABLE 1

[a]Mean values were estimated from nine samples per trait.

| Category | Trait | Unit | Range (Mean[a]) or Color (RHS Colour Designation) |
|---|---|---|---|
| Foliar | Plant height | mm | 270-370(302) |
| Foliar | Plant spread | mm | 550-670(596) |
| Foliar | Plant habit | | Semi-upright |
| Foliar | Plant vigor | | Medium |
| Foliar | Mid-tier terminal leaflet length | mm | 70-110(87) |
| Foliar | Mid-tier terminal leaflet width | mm | 90-120(103) |
| Foliar | Mid-tier terminal leaflet, margin type | | Serrate to Crenate |
| Foliar | Mid-tier terminal leaflet, base shape | | Obtuse |
| Foliar | Petiole length | mm | 190-245(222) |
| Foliar | Petiole, attitude of hairs | | Horizontal |
| Petiole | Petiole, color | color code | Strong Yellow Green (145 A) |
| Foliar | Stipule core color | color code | Strong Yellow Green (144 A) |
| Foliar | Stipule margin color | color code | Moderate Olive Green (137 A) |
| Foliar | Stolons/nursery mother plant | count | 13-15(14.5) |
| Foliar | Stolon color | color code | Strong Red (51 A) |
| Foliar | Stolon, average length | m | 1.25 meters |
| Foliar | Stolon, surface texture | | Smooth |
| Foliar | Leaf, average size | | Medium |
| Foliar | Leaf, blistering | | Medium |
| Foliar | Leaf, glossiness | | Medium |
| Foliar | Leaf color, adaxial | color code | Moderate Olive Green (147A) |
| Foliar | Leaf color, abaxial | color code | Moderate Yellow Green (147 B) |

TABLE 1-continued

[a]Mean values were estimated from nine samples per trait.

| Category | Trait | Unit | Range (Mean[a]) or Color (RHS Colour Designation) |
|---|---|---|---|
| Foliar | Inflorescence, position in relation to foliage | | Above |
| | Pedicel, average length | m | 30 |
| | Pedicel, attitude of hairs | | Upwards |
| Flower | Petal number | count | 5-6(6) |
| Flower | Petal length | mm | 10-12(11) |
| Flower | Petal width | mm | 10-13(11) |
| Flower | Petal arrangement | | Overlapping |
| Flower | Calyx diameter | mm | 25-35(31) |
| Flower | Corolla diameter | mm | 20-25(23) |
| Flower | Sepal number | count | 10-12(12) |
| Flower | Calyx Color | color code | Moderate Olive Green (147 B) |
| Flower | Upper Petal Color | color code | White (NN155 D) |
| Flower | Lower Petal Color | color code | White (NN155 D) |
| Flower | Stamen number | count | 22-32(27) |
| Fruit | Achene Color | color code | Greenish Brilliant Yellow (4 A) |
| Fruit | Fruit length | mm | 43-55(50) |
| Fruit | Fruit width | mm | 37-45(41) |
| Fruit | Fruit size | | Large |
| Fruit | Fruit shape | | Cordate |
| Fruit | Fruit evenness of color | | Even or slightly uneven |
| Fruit | Fruit glossiness | | Medium |
| Fruit | Fruit, evenness of the surface | | Even or slightly uneven |
| Fruit | Fruit, width of band without achene | | Absent or narrow |
| Fruit | Fruit, attitude of sepals | | Upwards |
| Fruit | Fruit, position of achenes | | Below surface |
| Fruit | Fruit, position of calyx attachment | | Level with fruit |
| Fruit | Fruit, adherence of calyx to fruit | | Strong |
| Fruit | Size of hollow core | mm | 3-13(7) |
| Fruit | External Fruit (exterior) color | color code | Vivid Reddish Orange (42 A) |
| Fruit | Fruit flesh color | color code | Light Yellowish Pink (36 A) |
| Fruit | Fruit core color | color code | Strong Yellowish Pink (37 A) |
| Fruit | Fruit size | g/fruit | 26-42(33) |

In Santa Maria, California, with a normal late May planting time, early flowering is early July, and the beginning of fruit ripening on those early flowers is 30 days post-flowering.

Disease Resistance

Marker-assisted selection was employed to identify individuals predicted to be heterozygous or homozygous for the dominant (favorable) alleles for a Fusarium wilt resistance (FW1) locus and the PERPETUAL FLOWERING (PF) locus. The genotypes predicted by PF- and FW-linked SNPs for 'UC Eclipse' were PFPF and FW1fw1. The predicted genotypes were confirmed with a 50,000 Aximo SNP array (Hardigan et al, 2020, supra).

The dominant FW1 allele confers resistance to *Fusarium* wilt race 1, cause by *Fusarium oxysporum* f.sp. *fragariae*. *Fusarium* resistance was further tested by three years of replicated testing of bare-root plants artificially inoculated with AMP132, a race 1 isolate of the pathogen.

'UC Eclipse' and comparison cultivars were evaluated for resistance to *Fusarium* wilt, *Verticillium* wilt, *Phytophthora* crown rot, and *Macrophomina* charcoal rot in fumigated fields using well established artificial inoculation protocols. 'UC Eclipse' was selected for resistance to *Fusarium* wilt and *Verticillium* wilt in 2019-20, 2020-21, and 2021-22 disease resistance screening nurseries. The disease score EMMs and statistics presented below were estimated from four replicates per hybrid per year among 243 to 262 hybrids (selection candidates) per year (Table 2).

'UC Eclipse' is resistant to *Fusarium* wilt (Table 2). The mean resistance score for this cultivar ($\bar{y}$=1.2) was not significantly different from the mean resistance scores for the resistant comparison cultivars, which were the short-day cultivar 'Fronteras', U.S. Plant Pat. No. 26,709, ($\bar{y}$=1.1; p=0.78) and the day-neutral cultivar 'San Andreas', U.S. Plant Pat. No. 19,975, ($\bar{y}$=1.2; p=0.91). 'UC Eclipse', 'Fronteras', and 'San Andreas' are heterozygous for the dominant *Fusarium* wilt race 1 resistance gene FW1.

*Verticillium* wilt resistance is quantitative in strawberry. Over three years of replicated testing, 'UC Eclipse' was found to be moderately resistant to *Verticillium* wilt ($\bar{y}$=2.1; Table 2). The strength resistance was not significantly different from 'UCD Finn' ($\bar{y}$=3.0; p=0.11), 'San Andreas' ($\bar{y}$=1.3; p=0.26), or 'UCD Mojo' ($\bar{y}$=2.0; p=0.78).

Phytophthora crown rot (PhCR) resistance is also quantitative in strawberry. Over three years of replicated testing, 'UC Eclipse' was found to be moderately susceptible to PhCR ($\bar{y}$=2.8; Table 2). The strength of resistance for 'UC Eclipse' was not significantly different from 'San Andreas' ($\bar{y}$=1.8; p=0.18), 'UCD Finn' ($\bar{y}$=3.1; p=0.69), or 'UCD Mojo' ($\bar{y}$=3.1; p=0.65).

Macrophomina charcoal rot (MCR) resistance was also assessed. None of the cultivars in this test were resistant to MCR (Table 2).

TABLE 2

*Fusarium* wilt, *Verticillium* wilt, *Phytophthora* crown rot, and *Macrophomina* charcoal rot resistance score[a] estimated-marginal means (EMMs) for 'UC Eclipse' and comparison cultivars observed in 2019-20, 2020-21, and 2021-22 field studies. The comparison cultivars are 'UCD Finn', 'UCD Mojo', 'San Andreas', and 'Monterey' (U.S. Plant Pat. No. 19,767).

| Disease[b] | Comparison Cultivar | UC Eclipse EMM | Comparison Cultivar EMM | t | p |
|---|---|---|---|---|---|
| *Fusarium* Wilt | UCD Finn | 1.2 | 3.8 | −5.32 | <0.0001 |
| | UCD Mojo | | 2.1 | −1.81 | 0.08 |
| | San Andreas | | 1.2 | 0.12 | 0.91 |
| | Monterey | | 3.4 | −4.39 | <0.0001 |
| *Verticillium* | UCD Finn | 2.1 | 3.0 | −1.62 | 0.11 |
| | UCD Mojo | | 2.0 | 0.28 | 0.78 |
| | San Andreas | | 1.3 | 1.14 | 0.26 |
| | Monterey | | 2.4 | −0.44 | 0.66 |
| *Phytophthora* | UCD Finn | 2.8 | 3.1 | −0.41 | 0.69 |
| | UCD Mojo | | 3.1 | −0.46 | 0.65 |
| | San Andreas | | 1.8 | 1.37 | 0.18 |
| | Monterey | | 3.1 | −0.37 | 0.71 |
| *Macrophomina* | UCD Finn | 4.4 | 5.2 | −1.14 | 0.26 |
| | UCD Mojo | | 3.5 | 1.30 | 0.20 |
| | San Andreas | | 4.7 | −0.38 | 0.71 |
| | Monterey | | 4.4 | −0.05 | 0.96 |

[a]The ordinal symptom rating scales were identical for each disease: 1 = highly resistant, 2 = moderately resistant, 3 = moderately susceptible, 4 = susceptible, and 5 = highly susceptible.
[b]The fungal pathogens causing these diseases are *Fusarium oxysporum* f. sp. *fragariae* (*Fusarium* wilt), *Verticillium dahliae* (*Verticillium* wilt), *Phytophthora cactorum* (*Phytophthora* crown rot), and *Macrophomina phaseolina* (*Macorphomina* charcoal rot).

Photoperiod Insensitive Phenotype

The dominant PF allele is necessary for photoperiod-insensitive flowering in cultivated strawberry. Although it is dominant (when plants are categorically classified as short-day or day-neutral), quantitative differences were observed in the strength and consistency of flowering between PFPF and PFpf hybrids in on-farm trials and selected both for advancement in the summer-plant breeding pipeline. Although PF homozygotes were generally perceived as less productive than heterozygotes; the opposite was found in summer-plant production systems. 'UC Eclipse' emerged from that selection work and significantly out-yielded other selection candidates and comparison cultivars over years and farms.

The predicted photoperiod insensitive phenotype of 'UC Eclipse' was confirmed through three years of on-farm testing. 'UC Eclipse' consistently flowered and fruited throughout the commercial summer-plant growing seasons in Oxnard (34.2° N), Lompoc (34.6° N), and Santa Maria (35.0° N) where daylengths range from 9.8 to 14.5 hours.

Field Evaluations

Three seasons of advanced testing of selected summer-plant hybrids originating from the 2016-17 breeding cycle were tested to further evaluate 'UC Eclipse' on nine farms in California. The bare-root clones for advanced testing were propagated in low-elevation nurseries using standard practices and post-harvest chilling treatments optimized for the summer-plant market segment. Clones for the first year of testing (Phase I in 2018-19) were produced in Winters, California. Clones for subsequent years of testing (Phase II in 2019-20 and 2020-21 and Phase III in 2021-22) were produced in commercial low-elevation nurseries in Manteca, CA. Clones were harvested in January, trimmed, and stored at −2° C. until planting in the summer.

Advanced testing was performed over three years. Testing started with 25 different Phase I hybrids on a single farm in Santa Maria in 2018-19. Nine hybrids were selected for Phase II testing on a single Santa Maria farm in 2019-20, and two Santa Maria farms in 2020-2021. Two hybrids were selected for Phase III testing on three farms in Santa Maria, Ventura, and Lompoc in 2021-22. Hybrids were grown in two 20-plant plots in Phase I and II and one 500-1,000 plant strip in Phase III (yield data were collected from two 50-plant blocks within each 500-1,000 plant strip). Over the course of advanced testing (Phase I-III), yield data were collected from 84 20- or 50-plant plots and seven summer-plant year×location environments. Clones were planted between 15 May to 15 June in Santa Maria and 1 to 15 July in Oxnard. The number of harvests ranged from 14 to 26 in each environment. Fruits were harvested following commercial harvest schedules. Selection was applied for fruit yield, size, and firmness, total soluble solid content or Brix (TSS=° Br), and titratable acidity (TA) among Phase I-III hybrids.

Fruit Yield

'UC Eclipse' was selected for fruit yield, size, and firmness. Yield data were collected from seven different on-farm yield trials grown under commercial summer-plant production and harvest practices. The estimated marginal means (EMMs) and test statistics for cumulative marketable fruit yield were estimated from 14 to 26 harvests per trial (Table 3). Hence, the yield differences across trials were partially caused by differences in commercial planting and harvest windows.

The cumulative marketable fruit yields of 'UC Eclipse' ranged from 27,109 to 79,399 lb/a across seven Phase I, II, or III trials (Table 3). 'UC Eclipse' yields were 14,787 lb/a greater than the three comparison cultivars over years and farms (a 54.0% yield increase over 'Portola'). The yield for 'UC Eclipse' across trials ($\bar{y}$=65,215 lb/a) was significantly greater than 'Portola' ($\bar{y}$=42,253 lb/a; t=2.5; p=0.02), 'LCD Finn' ($\bar{y}$=38,098 lb/a; t=2.8; p=0.01), and 'UCD Mojo' ($\bar{y}$=642 lb/a; t=2.5; p=0.02) (Table 3).

TABLE 3

Yield and fruit quality traits for 'UC Eclipse' and comparison cultivars grown on farms in coastal California over three years (2019-2021) under conventional and organic summer-plant production systems[a].

| Trait[a] | Comparison Cultivar | UC Eclipse EMM | Comparison Cultivar EMM | t[b] | p-value[c] |
|---|---|---|---|---|---|
| Yield (lb/acre) | Portola | 65,215 | 42,254 | 2.5 | 0.02 |
| | UCD Finn | | 38,098 | 2.9 | 0.01 |
| | UCD Mojo | | 41,642 | 2.5 | 0.02 |
| Size (g/fruit) | Portola | 30.2 | 26.3 | 6.0 | <0.0001 |
| | UCD Finn | | 24.0 | 8.9 | <0.0001 |
| | UCD Mojo | | 26.5 | 6.4 | <0.0001 |
| Firmness (g) | Portola | 315.4 | 302.1 | 2.1 | 0.07 |
| | UCD Finn | | 384.6 | −9.8 | <0.0001 |
| | UCD Mojo | | 384.3 | −9.8 | <0.0001 |
| Brix (°Bx) | Portola | 7.5 | 8.0 | −3.8 | 0.01 |
| | UCD Finn | | 8.4 | −6.4 | 0.002 |
| | UCD Mojo | | 8.5 | −7.5 | 0.001 |
| TA (%) | Portola | 0.7 | 0.8 | −3.1 | 0.03 |
| | UCD Finn | | 0.6 | 6.4 | 0.01 |
| | UCD Mojo | | 0.8 | −1.2 | 0.31 |
| °Bx/TA | Portola | 10.1 | 10.1 | −0.1 | 0.92 |
| | UCD Finn | | 13.2 | −10.3 | 0.001 |
| | UCD Mojo | | 11.1 | −3.5 | 0.03 |

[a]Cumulative marketable fruit yields were estimated from fruit harvested on commercial schedules (twice weekly) over the entire summer-plant growing season on each farm. Fruit firmness, Brix, and titratable acidity were measured from multiple fruit/replication sampled from two harvests/trial. EMMs and test statistics were estimated from observations across seven on-farm yield trials.
[b]t-statistics for linear contrasts between the EMMs for 'UC Eclipse' and comparison cultivars.
[c]The probability of a greater t-statistic by chance for the null hypothesis of no difference between two EMMs.

Fruit Quality

'UC Eclipse' meets the fruit quality and shelf life standards of cultivars developed for long-distance shipping in coastal California (Table 3). Statistics for the linear contrasts between 'UC Eclipse' and comparison cultivars across seven on-farm yield trials are shown in Table 3. The following paragraphs highlight the most important comparisons and differences.

'UC Eclipse' fruit were significantly larger than 'Portola', 'UCD Finn', and 'UCD Mojo'. The size consistency of 'UC Eclipse' throughout the growing season.

'UC Eclipse' fruit was significantly firmer than 'Portola' and significantly softer than 'UCD Finn' and 'UCD Mojo'. The firmness of 'UC Eclipse' exceeded the threshold necessary for long shelf life cultivars.

The total soluble solids (° Bx) and titratable acidity (TA) of 'UC Eclipse' were significantly lower than the comparison cultivars; however, the ° Bx/TA (sugar-to-acid) ratio for 'UC Eclipse' was not significantly different from 'Portola'; hence, the perceived sweetness of these cultivars was essentially the same.

Minimal declines were observed in the deterioration of firmness and other fruit quality traits over 14 clays of post-harvest cold storage. No significant differences were observed between cultivars over days post-harvest for leakage, gloss, mold, or other post-harvest traits.

Fruit Shelf Life

'UC Eclipse' meets the need for a high yielding long shelf life cultivar for summer-plant and 'off-season' production in high latitude environments outside of California, e.g., Canada and Northern Europe. 'UC Eclipse' is also suitable in any open-field or protected-culture production system where photoperiod insensitive flowering is needed, particularly for protected-culture production systems where clones are planted in warmer months of the year and under warm conditions indoors.

Fruit Production Characteristics—Field Trials

Statistics are shown for linear contrasts between 'UC Eclipse' and comparison cultivar EMMs for individual trials (year×location combinations) to highlight variation in planting and harvest dates, the number of harvests, and production practices (Table 4). 'UC Eclipse' outyielded 'Portola', 'UCD Finn', and 'UCD Mojo' in every trial by 10.3 to 69.1% (Table 4). The yield differences were statistically significant (p<0.05) for 16 of the 19 trial×comparison cultivar comparisons (Table 4).

TABLE 4

Cumulative marketable yields of 'UC Eclipse' and comparison cultivars grown on farms in coastal California over three years (2019-2021) under conventional and organic summer-plant production systems.

| Location[a] | Year | UC Eclipse Yield (lb/a) | Comparison Cultivar | Comparison Cultivar Yield (lb/a) |
|---|---|---|---|---|
| Nipomo | 2019 | 65,608 | Portola | 47,314 |
| | | | UCD Finn | 50,689 |
| | | | UCD Mojo | 58,831 |
| Ventura | 2019 | 27,109 | Portola | 19,759 |
| | | | UCD Finn | 20,825 |
| | | | UCD Mojo | 22,239 |
| Nipomo | 2020 | 54,656 | Portola | 16,877 |
| | | | UCD Finn | 30,180 |
| | | | UCD Mojo | 27,386 |
| Nipomo | 2020 | 43,944 | Portola | 29,748 |
| | | | UCD Finn | 36,717 |
| | | | UCD Mojo | 35,600 |
| Santa Maria | 2020 | 29,402 | Portola | 19,901 |
| | | | UCD Finn | 22,570 |
| | | | UCD Mojo | 22,122 |
| Nipomo | 2021 | 79,399 | Portola | 52,989 |
| | | | UCD Finn | 47,418 |
| | | | UCD Mojo | 64,962 |
| Lompoc | 2021 | 37,097 | Portola | 30,549 |

| Location[a] | Yield Gain (lb/a) | Yield Gain (%) | t[b] | p-value[c] |
|---|---|---|---|---|
| Nipomo | 18,294 | 27.9 | 3.3 | 0.02 |
| | 14,920 | 22.7 | 2.7 | 0.04 |
| | 6,777 | 10.3 | 1.2 | 0.28 |
| Ventura | 7,350 | 27.1 | 3.1 | 0.03 |
| | 6,284 | 23.2 | 2.6 | 0.05 |
| | 4,870 | 18.0 | 2.0 | 0.10 |
| Nipomo | 37,778 | 69.1 | 117.7 | <0.0001 |
| | 24,476 | 44.8 | 76.3 | <0.0001 |
| | 27,269 | 49.9 | 85.0 | <0.0001 |
| Nipomo | 14,195 | 32.3 | 9.8 | <0.0001 |
| | 7,226 | 16.4 | 4.9 | 0.0004 |
| | 8,343 | 19.0 | 5.8 | 0.0001 |
| Santa Maria | 9,501 | 17.4 | 5.4 | 0.01 |
| | 6,922 | 12.7 | 3.9 | 0.03 |
| | 7,370 | 13.5 | 4.1 | 0.03 |
| Nipomo | 26,410 | 33.3 | 16.8 | <0.0001 |
| | 31,981 | 40.3 | 28.0 | <0.0001 |

TABLE 4-continued

Cumulative marketable yields of 'UC Eclipse' and comparison cultivars grown on farms in coastal California over three years (2019-2021) under conventional and organic summer-plant production systems.

| | | | | |
|---|---|---|---|---|
| | 14,437 | 18.2 | 23.4 | <0.0001 |
| Lompoc | 6,548 | 17.7 | 4.4 | 0.14 |

[a]The Santa Maria 2020 trial was under organic production. The other trials were under conventional production. The only comparison cultivar tested in the Lompoc 2021 trial was 'Portola'. Trials were grown on two different Nipomo farms in 2020, one with Greg France (Mar Vista Farms) and another with Christopher Winterbottom (Good Farms).
[b]t-statistics for linear contrasts between the EMMs for 'UC Eclipse' and comparison cultivars.
[c]The probability of a greater t-statistic by chance for the null hypothesis of no difference between two EMMs.

'UC Eclipse' produces significantly higher marketable fruit yields than 'Portola', 'UCD Finn', and 'UCD Mojo'. The cumulative marketable fruit yields of 'UC Eclipse' exceeded 'Portola', 'UCD Finn', and 'UCD Mojo' by 54% over years, locations, and production systems (Tables 3 and 4).

'UC Eclipse' is resistant to *Fusarium* wilt race 1, a disease caused by isolates of *Fusarium oxysporum* f.sp. *fragariae*. 'Portola' and 'UC Eclipse' carry the dominant *Fusarium* wilt resistance gene FW1. 'UCD Finn' and 'UCD Mojo' are susceptible to *Fusarium* wilt race 1 and homozygous for the recessive (susceptible) allele fw1.

'UC Eclipse' produces fruit with outstanding size and firmness throughout the growing season, whereas 'Portola' fruit tend to become smaller and softer as the season progresses.

'UC Eclipse' is well adapted to summer-production systems and environments in California, consistently flowers over the full range of day lengths encountered in California, and is homozygous for the PF allele. Although a single copy of the PF allele is sufficient for photoperiod insensitive flowering, on-farm testing has empirically shown that PF homozygotes frequently outperform heterozygotes in summer-plant environments where temperatures are typically greater than those encountered in fall-planted day-neutral environments in California.

'UC Eclipse' is thus a highly productive *Fusarium* wilt-resistant cultivar for the summer-plant segment. 'UC Eclipse' can be used for fresh market and processing purposes.

What is claimed is:

1. A new and distinct cultivar of strawberry plant named 'UC Eclipse', substantially as described and illustrated herein.

* * * * *